United States Patent [19]

Post et al.

[11] Patent Number: 5,122,458

[45] Date of Patent: Jun. 16, 1992

[54] USE OF A BGH GDNA POLYADENYLATION SIGNAL IN EXPRESSION OF NON-BGH POLYPEPTIDES IN HIGHER EUKARYOTIC CELLS

[75] Inventors: Leonard E. Post; Daniel P. Palermo; Darrell R. Thomsen, all of Kalamazoo, Mich.; Fritz M. Rottman, Pepper Pike; Edward C. Goodwin, Cleveland Heights, both of Ohio; Richard P. Woychik, Knoxville, Tenn.

[73] Assignee: The Upjohn Company, Kalamazoo, Mich.

[21] Appl. No.: 295,967

[22] Filed: Jan. 11, 1989

Related U.S. Application Data

[63] Continuation-in-part of Ser. No. 758,517, Jul. 26, 1985, abandoned, which is a continuation-in-part of Ser. No. 668,764, Nov. 6, 1984, abandoned, which is a continuation-in-part of Ser. No. 644,306, Aug. 24, 1984, abandoned.

[51] Int. Cl.$^5$ .................... C12N 15/11; C12N 15/12; C12N 15/85; C12P 21/00
[52] U.S. Cl. .................... 435/69.1; 435/69.2; 435/240.1; 435/240.2; 435/320.1; 536/27; 935/6; 935/34; 935/70
[58] Field of Search .................... 435/172.1, 172.3, 91, 435/243, 240.1, 240.2, 69.1, 69.2, 320.1; 536/27; 935/6, 10, 14, 11, 32, 34, 61, 70, 71

[56] References Cited

U.S. PATENT DOCUMENTS

| | | | |
|---|---|---|---|
| 4,399,216 | 8/1983 | Axel et al. | 435/6 |
| 4,405,712 | 9/1983 | Vande Woude et al. | 435/5 |

FOREIGN PATENT DOCUMENTS

| | | | |
|---|---|---|---|
| 0112012 | 6/1984 | European Pat. Off. | 435/172.3 |

OTHER PUBLICATIONS

Sasavage, N. L., et al., "Use of Oligodeoxynucleotide Primers to Determine Poly(adenylic acid) Adjacent . . . Bovine Growth Hormone Messenger Ribonucleic Acid", Biochemistry, vol. 19, pp. 1737-1743 (1980).

Fitzgerald, M., et al., "The Sequence 5'-AAUAAA-3' Forms Part of the Recognition . . . SV40 mRNAs", Cell, vol. 24, pp. 251-260 (Apr. 1981).

Woychik, R. P., et al., "Cloning & nucleotide sequencing of the bovine growth hormone gene", Nucleic Acids Research, vol. 10, No. 22, pp. 7197-7210 (1982).

Woychik, R. P., et al., "Requirement for the 3' flanking region of the bovine growth hormone gene for accurate polyadenylylation", Proc. Natl. Acad. Sci., USA, vol. 81, pp. 3944-3948 (Jul. 1984).

Rottman, F. M., et al., "Role of Post-Transcriptional mRNA Modification in the Maintenance of Eucaryotic mRNA Levels", Chem. Abstr. vol. 102, 1349g (1985) of GENE EXPRESSION, Alfred Benzon Symposium 19, pp. 279-290 (1984).

Pennica, D., et al., "Cloning and expression of human tissue-type plasminogen activator cDNA in E. coli", Nature, vol. 301, pp. 214-221 (Jan. 20, 1983).

Southern, P. J. & P. Berg, "Transformation of Mammalian Cells to Antibiotic Resistance with a Bacterial Gene Under Control of the SV40 Early Region Promoter", Jr. of Molecular & Applied Genetics, vol. 1, pp. 327-341 (1982).

Stinski, M. F., et al., "Organization and Expression of the Immediate Early Genes of Human Cytomegalovirus", Jr. of Virology, vol. 46, No. 1, pp. 1-14 (Apr. 1983).

Stenberg, R. M., et al., "Structural Analysis of the Major Immediate Early Gene of Human Cytomegalovirus", Jr. of Virology, vol. 49, No. 1, pp. 190-199 (Jan. 1984).

Thomsen, D. R., et al., "Promoter-regulatory region of the major immediate early gene of human cytomegalovirus", Prov. Natl. Acad. Sci. USA, vol. 81, pp. 659-663 (Feb. 1984).

Hsiung, N., et al., "Efficient Production of Hepatitis B Surface Antigen Using a Bovine Papilloma Virus-Metallothionein Vector", Jr. of Molecular & Applied Genetics, vol. 2, pp. 497-506 (1984).

Subramani, S., et al., "Expression of the Mouse Dihydrofolate Reductase Complementary Deoxyribonucleic Acid in Simian Virus 40 Vectors", Molecular & Cellular Biology, vol. 1, pp. 854-864 (Sep. 1981).

Rao, R. N. & S. G. Rogers, "Plasmid pKC7: A Vector Containing Ten Restriction Endonuclease Sites Suitable for Cloning DNA Segments", GENE, vol. 7, pp. 79-82 (1979).

Urlaub, G & L. A. Chasin, "Isolation of Chinese ham- (List continued on next page.)

*Primary Examiner*—James Martinell
*Attorney, Agent, or Firm*—Mark DeLuca; Robert A. Armitage

[57] ABSTRACT

The present invention relates to the use of the polyadenylation signal from the gene for bovine growth hormone to achieve a high level of expression of peptides in eukaryotic cells. Accordingly, the present invention provides a recombinant DNA compound comprising: a first nucleotide sequence which contains a promoter capable of initiating transcription of a gene; a second nucleotide sequence which encodes a gene for a polypeptide other than bovine growth hormone, including genomic and other intron containing forms thereof; a third nucleotide sequence which contains a bovine growth hormone polyadenylation signal; and a fourth nucleotide sequence which optionally contains a selectable marker. The first, second and third sequences are operably linked in sequence to form a functional genetic unit capable of being expressed. The fourth sequence, which is optionally provided, is useful for determining whether or not the DNA of the present invention has been incorporated into a living cell.

11 Claims, No Drawings

OTHER PUBLICATIONS ster cell mutants deflicient in dihydrofolate reductase activity", Proc. Natl. Acad. Sci. USA, vol. 77, No. 7, pp. 4216–4220 (Jul. 1980).

Graham, F. L., et al., "Transformation of Mammalian Cells with DNA Using the Calcium Technique", Introduction of Macromolecules Into Viable Mammalian Cells (publisher Alan R. Liss, Inc., New York, N.Y.), pp. 3–25.

Pfarr, D. S., et al., "Differential Effects of Polyadenylation Regions on Gene Expression in Mammalian Cells", DNA, vol. 5, No. 2, pp. 115–122 (1986).

Higgs, D. R., et al., "α-Thalassaemia caused by a polydenylation signal mutation", Nature, vol. 306, pp. 398–400 (Nov. 24, 1983).

Hunt, L. T. & M. O. Dayhoff "9–Hormones and Active Peptides", Atlas of Protein Sequence & Structure (ed. M. O. Dayhoff, Natl. Biomed. Res. Fnd., Washington, DC), vol. 5, Suppl. 2, pp. 113–139 (1976).

Lingappa, V. R., et al., "Nascent prehormones are intermediates in the biosynthesis of authentic bovine pituitary growth hormone and prolactin", Proc. Natl. Acad. Sci. USA, vol. 74, No. 6, pp. 2432–2436 (Jun. 1977).

USE OF A BGH GDNA POLYADENYLATION SIGNAL IN EXPRESSION OF NON-BGH POLYPEPTIDES IN HIGHER EUKARYOTIC CELLS

CROSS REFERENCE TO RELATED APPLICATIONS

This application is a continuation-in-part application Ser. No. 758,517 filed July 26, 1985, abandoned which is a continuation-in-part of Ser. No. 668,764 filed Nov. 6, 1984, now abandoned, which is a continuation-in-part of Ser. No. 644,306 filed Aug. 24, 1984, now abandoned.

BACKGROUND OF THE INVENTION

The present invention provides novel compositions of matter and novel methods of using these compositions of matter. In particular, the present invention provides novel recombinant DNA (rDNA) compounds and methods for incorporating these novel compounds into the expressed genetic material of cells and cell lines, whereby novel cells and cell lines are thereby produced and comprise yet another element of the invention herein. Most particularly, the present invention relates to the incorporation of recombinant DNA compounds into the expressed genetic material of higher eukaryotic cells for expression of pre-selected polypeptides.

Methods of synthesis of recombinant DNA compounds are well known in the art. Moreover, these techniques have been extensively cataloged. Refer, for example, to T. Maniatis, et al., "Molecular Cloning: A Laboratory Manual," Cold Spring Harbor Laboratory Cold Spring Harbor, N.Y. (1982). Also for a general discussion of recombinant DNA compounds and their synthesis and use in molecular biology, refer to J.D. Watson, et al., "Recombinant DNA: A Short Course," Scientific American Books, New York, N.Y. (1983), and the extensive bibliography of references cited therein.

DNA compounds in accordance with the present invention are those biologically useful polymers of deoxyribonucleic acid linked together by 5'-3' phosphodiester bonds between the sugar (deoxyribose) and phosphate groups. The DNA polymers are those composed of repeating nucleotide units and, as disclosed herein are capable of existing in the double helix configuration wherein the paired guanine/cytosine (G/C) and adenine/thymine (A/T) bases form hydrogen bonds stabilizing the double helix.

DNA compounds are known to exist in all or essentially all living cells. These DNA compounds when incorporated into the expressed genetic material of cells, e.g., properly incorporated as elements of genes, plasmids, and chromosomes, are capable of transcribing into messenger ribonucleic acid (mRNA) the ordered base pair sequences of the DNA. The process of transcription into RNA is part of the process which enables polypeptide and/or protein synthesis within living cells to be accomplished. The techniques of molecular biology now permit recombinant DNA compounds to be incorporated into the expressed genetic material of living cells for the purpose of transcribing into messenger RNA coding for pre-selected polypeptides other than those which a cell might be capable of synthesizing prior to the incorporation or permit the cell to synthesize its natively-produced polypeptides at much higher expression levels.

Molecular biology research often begins by the isolation and characterization of DNA compounds from native sources. For example, a DNA compound has been isolated from the adult bovine pituitary which transcribes into messenger RNA the base pair coding which directs the synthesis of bovine growth hormone or bGH. The isolation and characterization of this DNA compound is described in European published patent application 0112012, published June 27, 1984. Because this DNA compound was derived from the bovine pituitary gene responsible for bGH expression, such a compound is commonly referred to as genomic DNA or gDNA.

In general, messenger RNA derived from this gDNA by transcription can then be copied into DNA utilizing reverse transcriptase enzymes. This copying of an RNA base sequence onto DNA yields a DNA compound commonly referred to as copy DNA or cDNA. For mammalian genes, the sequence of cDNA often differs from the sequence of gDNA coding for the same polypeptide or protein in that the gDNA often contains introns or non-polypeptide coding sequences in addition to the codons. Refer, for example, to the known bGH gDNA containing four such introns between the 5' and 3 ends. Those ordered gDNA sequences with ordered counterparts on this mRNA transcribed there. from are, accordingly, often referred to as "exons".

Genes capable of expression contain flanking sequences beyond the exons (the portions of DNA that are transcribed onto messenger RNA) which do not code for messenger RNA but are nonetheless essential to the transcription process. Upstream (above the 5' end) from the site where messenger RNA transcription begins is a DNA sequence responsible for promotion or initiation of transcription which is commonly referred to as the "promoter"In most eukoryotic cells, a region of DNA downstream (below the 3' end) from the last exon is responsible for the addition to messenger RNA of a long sequence of adenine-containing nucleotides which are added after transcription is completed. This region thus signals the addition of a "poly-adenine tail" also known as the polyadenylation of the messenger RNA.

For some proteins certain of the requirements for this poly. adenylation signal are known. See, for example, R.P. Woychik, et al., "Requirement for the 3' Flanking Region of the Bovine Growth Hormone Gene for Accurate Polyadenylation", Proc. Natl. Acad. Sci. USA 81:3944–3948 (July 1984) Also, the nucleotide sequence AATAAA characterizes the polyadenylation signal at a location 11 to 30 nucleotides upstream (towards the 5' end) from the 3' end of the gene. Refer to D.R. Higgs, et al., Nature 306:398–400 (Nov. 24, 1983) and references cited therein.

The present specification describes a method for utilizing a bGH polyadenylation signal in conjunction with DNA especially cDNA. coding for a pre-selected polypeptide other than bGH as a means of obtaining expression of the pre-selected polypeptide in a higher eukaryatic cell.

INFORMATION DISCLOSURE

The identification and characterization of bGH gDNA is known. See European published application 0112012, published on June 27, 1984. Certain of the requirements for accurate polyadenylation of bovine growth hormone are similarly known. See R.P. Woychik, et al., Proc. Natl. Acad. Sci. USA 81:3944–3948 (July 1984).

Sasavage et al.: Biochemistry 19:1737 (1980) teaches a technique based on chain termination method of Sanger, et al., 1977, for screening an enriched population of poly(A) mRNA for specific initiation of cDNA synthesis and obtained the complete 3'-nontranslated sequence of bGH mRNA using reverse transcriptase directed cDNA synthesis to enriched bGH mRNA. Sasavage made comparisons of bGH 3' untranslated region to rat and human growth hormone sequences and concluded that the role of the 3' untranslated region is still unclear. Although Sasavage et al. obtained the complete 3' untranslated region they concluded that the role of this region is still unclear.

Fitzgerald et al.: Cell 24:251 (1981), using late SV40 mRNAs, established that the AATAAA sequence near the 3' end of eucaryotic mRNAs is required for poly(A) addition, and speculated that this is probably an almost universal component.

Woychik et al.: Nucleic Acids Res., 10:7197 (1982) teach the genomic nucleotide sequence of the bovine growth hormone gene isolated from a bovine genomic library. The sequence includes the 3' untranslated region of the bGH gene. Analysis of the homology of this gene with those of the growth hormone gene sequences derived from human and rat genes is disclosed. The presence of the hexanu. cleotide sequence AATAAA is noted and its role in polyadenylation of messenger RNA is indicated.

Woychik et al.: Pro. Natl. Acad. Sci, USA, 81:3944 (1984) teaches the effect of nucleotides extending 3' to the polyadenylation site in polyadenylation of bGH mRNA. Woychik et al. found that the gene contained 84 base pairs of its own 3' flanking sequence poly. adenylates in the same site as with the wild type mRNA, and that the genes with fewer than 84 base pairs 3 to the polyadenylation site resulted in polyadenylation at sites different from that found in wild type mRNA.

Rotman et al.: Chem. Abstr. 102:1349g (1985) of Alfred Benzon Symp. 19:279-290 (1984), teaches the role of post transcriptional regulatory events in gene expression. Specifically, Rotman et al. examine the role of methylation in the processing of normal cellular mRNAs. The plasmid pSVB3/BA which contains the bGH gene containing the polyadenylation signal and under the control of the late SV40 promoter is described. Cells were transfected with either bGH cDNA clone or a prolactin cDNA clone and resulting expression compared. Studies of the polyadenylation signal of the respective cDNA clones reveal that bGH mRNA have a single site for polyadenylation, whereas there were three distinct polyadenylation sites in the prolactin message. It is noted that the bGH expression was at a high level.

SUMMARY OF THE INVENTION

The present invention relates to the use of a polyadenylation signal derived from the gene for bovine growth hormone to obtain high level expression of recombinant genes which code for polypeptides other than bovine growth hormone. Use of the polyadenylation signal from bovine growth hormone in a recombinant construction results in the high level expression of genes linked thereto.

The present invention particularly provides a circular recombinant DNA compound comprising:

a) a first nucleotide sequence which contains a promoter capable of initiating transcription of a gene;

b) a second nucleotide sequence which encodes a gene for a polypeptide other than bovine growth hormone, including genomic and other intron containing forms thereof;

c) a third nucleotide sequence which contains a bovine growth hormone polyadenylation signal; and d) a fourth nucleotide sequence which optionally contains a selectable marker.

The first, second and third sequences are operably linked in sequence to form a functional genetic unit. The promoter of the first sequence is linked to the second nucleotide sequence such that the promoter serves to regulate transcription of the gene found in the second sequence. The polyadenylation signal contained in the third sequence is sequentially linked to the second sequence and provides the information necessary to bring about the polyadenylation of the subsequently produced messenger RNA. Thus the first three sequences described above form a functional genetic unit capable of expressing a structural gene. The fourth sequence, which is optionally provided, is useful for determining whether or not the DNA of the present invention has been incorporated into a living cell. The marker genes utilized in the present invention, if present at all, need only be located within the circular DNA compound. They do not interact with the functional genetic unit described above, but instead they allow for the selection of cells containing the recombinant DNA compound.

The present invention additionally provides a method of using this recombinant DNA compound for expression of the pre-selected polypeptide.

Additionally, the present invention provides a higher eukoryote cell or cell line whose expressed genetic material comprises the recombinant DNA compound.

Furthermore, the present invention particularly provides a method of producing tPA which comprises culturing such a cell line in which the second nucleotide sequence of the recombinant DNA compound included in its expressed genetic material comprises the tPA cDNA.

DETAILED DESCRIPTION OF THE INVENTION

In accordance with the invention described above, the novel compounds, living cells and/or cell lines, and uses thereof all incorporate in a recombinant DNA compound a bovine growth hormone (bGH) polyadenylation signal. Bovine growth hormone (bGH) is a 191 amino acid polypeptide, synthesized initially as a pre-growth hormone containing a signal peptide of 26 amino acids. (See Hunt, L.T. and Dayhoff, M.O., 1976, In: Atlas of Protein Sequence and Structure, ed. M.0. Dayhoff, National Biomedical Research Foundation, Washington, DC, Vol. 5, Suppl. 2, pp. 113-139; and Lingappa. V.R., Devillers-Thiiery, A. and Blobel, G., 1977, Proc. Natl Acad. Sci. 74:2432-2436.) Using recombinant DNA procedures, a bGH genomic clone is now known and a genomic clone, designated pgGH2R2, is deposited in the permanent collection of the Northern Regional Research Laboratory (NRRL), U.S. Department of Agriculture Peoria, IL U.S.A. It was deposited in an E. coli HB101 host and its accession number in this repository is NRRL B-15154. Also deposited in an E. coli HB101 host is the bGH gDNA containing clone pgGH2R3 which has the accession number NRRL B-15155.

The bGH gDNA nucleotide sequence is known to oe essentially the following (nucleotides indicated by base A, T, G, or C):

AAAACCTATGGGGTGGGCTCTCAAGCTGAGACCCTGTGTGCACAGCCCTCTGGCTGGTGGCAGTGGAG

ACGGGATNNNATGACAAGCCTGGGGGACATGACCCCAGAGAAGGAACGGGAACAGGATGAGTGAGAGGAG

5c
GTTCTAAATTATCCATTAGCACAGGCTGCCAGTGGTCCTTGCATAAATGTATAGAGCACACAGGTGGGGG

5'
GAAAGGGAGAGAGAGAAGAAGCCAGG<u>GTATAAAAA</u>TGGCCCAGCAGGGACCAATTCCAGGATCCCAGGAC

−26
                                                                             Met Met Ala Ala
CCAGTTCACCAGACGACTCAGGGTCCTGTGGACAGCTCACCAGCT ATG ATG GCT GCA G gtaag ctcgctaaaatccctccattcgcgtgtcctaaaggggtaatgcggggggccctgccgatggatgtgttc agagctttgggctttagggcttccgaatgtgaacataggtatctacacccagacatttggccaagtttga aatgttctcagtccctggagggaagggtaggtgggggctggcaggagatcaggcgtctagctccctgggg −20
                        Gly Pro Arg Thr Ser Leu Leu Leu Ala
ccctccgtcgcggccctcctggtctctccctag GC CCC CGG ACC TCC CTG CTC CTG GCT −10                                                  1
Phe Ala Leu Leu Cys Leu Pro Trp Thr Gln Val Val Gly Ala Phe Pro Ala
TTC GCC CTG CTC TGC CTG CCC TGG ACT CAG GTG GTG GGC GCC TTC CCA GCC 10                                            20
Met Ser Leu Ser Gly Leu Phe Ala Asn Ala Val Leu Arg Ala Gln His Leu
ATG TCC TTG TCC GGC CTG TTT GCC AAC GCT GTG CTC CGG GCT CAG CAC CTG 30
His Gln Leu Ala Ala Asp Thr Phe Lys Glu Phe
CAT CAG CTG GCT GCT GAC ACC TTC AAA GAG TTT gtaagctcccgagggatgcgt cctaggggtggggaggcaggaagggtgaatccacaccccctccacacagtgggaggaaactgaggagtt cagccgtattttatccaagtagggatgtggttaggggagcagaaacgggggtgtgtggggtggggagggt tccgaataaggcggggaggggaaccgcgcaccagcttagacctgggtgggtgtgttcttcccccag 40
Glu Arg Thr Tyr Ile Pro Glu Gly Gln Arg Tyr Ser Ile Gln Asn Thr Gln
GAG CGC ACC TAC ATC CCG GAG GGA CAG AGA TAC TCC ATC CAG AAC ACC CAG 50                                       60
Val Ala Phe Cys Phe Ser Glu Thr Ile Pro Ala Pro Thr Gly Lys Asn Glu
GTT GCC TTC TGC TTC TCT GAA ACC ATC CCG GCC CCC ACG GGC AAG AAT GAG 70
Ala Gln Gln Lys Ser
GCC CAG CAG AAA TCA gtgagtggcaacctcggaccgaggagcaggggacctccttcatcctaa gtaggctgccccagctctccgcaccgggcctggggcggccttctccccgaggtggcggaggttgttggat ggcagtggaggatgatggtgggcggtggtggcaggaggtcctcgggcagaggccgaccttgcagggctgc Asp Leu Glu Leu Leu Arg Ile
cccaagcccgcggcacccaccgaccaccatctgccagcag GAC TTG GAG CTG CTT CGC ATC 80                          .              90   ↓↓ PstI (blunt end)
Ser Leu Leu Leu Ile Gln Ser Trp Leu Gly Pro Leu Gln Phe Leu Ser Arg
TCA CTG CTC CTC ATC CAG TCG TGG CTT GGG CCC <u>CTG CAG</u> TTC CTC AGC AGA 100                                       110
Val Phe Thr Asn Ser Leu Val Phe Gly Thr Ser Asp Arg Val Tyr Glu Lys
GTC TTC ACC AAC AGC TTG GTG TTT GGC ACC TCG GAC CGT GTC TAT GAG AAG 120
Leu Lys Asp Leu Glu Glu Gly Ile Leu Ala Leu Met Arg
CTG AAG GAC CTG GAG GAA GGC ATC CTG GCC CTG ATG CGG gtggggatggcgt tgtgggtcccttccatgctgggggggccatgcccgccctctcctggcttagccaggagaatgcacgt gggcttggggagacagatccctgctctctccctctttctagcagtccagccttgacccaggggaa accttttcccctttgaaacctccttcctcgcccttctccaagcctgtaggggagggtggaaaat ggagcgggcaggagggagctgctcctgagggcccttcggcctctctgtctctccctcccttggcag

```
                    130                                    140
Glu Leu Glu Asp Gly Thr Pro Arg Ala Gly Gln Ile Leu Lys Gln Thr
GAG CTG GAA GAT GGC ACC CCC CGG GCT GGG CAG ATC CTC AAG CAG ACC

150
Tyr Asp Lys Phe Asp Thr Asn Met Arg Ser Asp Asp Ala Leu Leu Lys
TAT GAC AAA TTT GAC ACA AAC ATG CGC AGT GAC GAC GCG CTG CTC AAG 160                             170
Asn Tyr Gly Leu Leu Ser Cys Phe Arg Lys Asp Leu His Lys Thr Glu
AAC TAC GGT CTG CTC TCC TGC TTC CGG AAG GAC CTG CAT AAG ACG GAG 180                       190    ↓↓ PvuII
Thr Tyr Leu Arg Val Met Lys Cys Arg Arg Phe Gly Glu Ala Ser Cys
ACG TAC CTG AGG GTC ATG AAG TGC CGC CGC TTC GGG GAG GCC AGC TGT
                                                     PvuII ↑↑

Ala Phe am
GCC TTC TAG TTGCCAGCCATCTGTTGTTTGCCCCTCCCCCGTGCCTTCCTTGACCCTG

↓3'
GAAGGTGCCACTCCCACTGTCCTTTCCTAATAAAATGAGGAAATTGCATCGC ATTGTCTG

AGTAGGTGTCATTCTATTCTGGGGGGTGGGGTGGGGCAGGACAGCAAGGGGGAGGATTGGGA

AGACAATAGCAGGCATGCTGGGGATGCGGTGGGCTCTATGGGTACCCAGGTGCTGAAGAA

TTGACCCGGTTCCTCCTGGG
```

Lower case letters correspond to intron sequences. The mRNA transcription initiation and termination positions are designated above as 5' and 3'. Finally, recognition sites for the restriction endonuclease PstI and PvuII are noted above (underlined), as well as the actual cleavage sites (cleavage occurs between the double arrows). PstI cleaves nucleotides as symmetrically yielding a DNA compound whose end contains four unpaired bases corresponding to the TGCA sequence of bGH gDNA. When these sequences are removed by a T4 DNA polymerase, the result is a blunt-ended DNA compound (i.e., eliminating unpaired or "sticky" ended terminal residues). The effective or PstI (Blunt-ended) cleavage site resulting is indicated by the downward arrows. Finally, the nucleotide sequence associated with polyadenylation, AATAAA is underlined.

In accordance with the present specification, the bGH poly. adenylation signal is a DNA nucleotide sequence whose functional center is located about the 3' end of the genomic bGH gene and which in the transcription of this bGH gene into messenger RNA, is capable of signaling polyadenylation (the addition of a long chain or "tail" of adenine-containing nucleotides) for the messenger RNA (mRNA). Accordingly, a bGH polyadenylation signal includes the nucleotides as in the genomic sequence from the 3' end to about 50 to about 500 nucleotides downstream (i.e., away from the 5' end) from the 3' end. More preferrably, however, the polyadenylation signal includes not more than about 70 such nucleotides downstream from the 3' end of bGH genomic DNA (gDNA). Upstream (i.e., towards the 5' end) the poly-adenylation signal preferably includes the genomic sequence from the 3' end to about 50 nucleotides upstream, but alternatively may include a substantially greater number of such upstream nucleotide bases. For example, the location of convenient cleavage sites for restriction endonucleases permits facile use of a substantially greater number of upstream nucleotides. Accordingly a polyadenylation signal can be represented as a DNA compound of the formula $$5' \leftarrow \lfloor \underline{UUUUUUUUU}\overline{DDDDDDDD} \rfloor \; \downarrow 3'$$

wherein the "U" again represents nucleotide sequences of bGH of DNA upstream from the 3' end and the "D" region represents nucelotides downstream from the 3' end.

In addition to the preferred embodiments set forth hereinabove, most preferably the bGH polyadenylation signal consists of the following nucleotide sequence:

```
5'                                                               3'   Formula 21
GTCCTTTCCTAATAAAATGAGGAAATTGCATCGCATTGTCTGAGTAGGTGTC
``` and any functional equivalent thereof. By functional equivalent is meant a compound comprising the above-identified nucleotide sequence which performs biologically in substantially the same manner as the compound represented by the above-identified nucleotide sequence but wherein one or more nucleotides have been modified, e.g., by substitution of one nucleotide for another.

This most preferred embodiment can be prepared by the general procedures described hereinabove, i.e., by digestion of the bGH gDNA and/or by chemical synthesis.

Within the parameters for the selection of a bGH polyadenylation signal as described above, the actual DNA compound comprising the signal can be prepared from bGH gDNA by cleavage with a known restriction endonuclease. Thereafter the DNA compound thereby prepared can be used as a signal after "pruning" or cleavage of several additional bGH polyadenylation nucleotides beyond those actually cleaved from the bGH gDNA by the restriction endonuclease. The techniques for using such endonucleases for accomplishing the pruning of DNA compounds are known in the art. See the references listed above.

Alternatively, additional nucleotides may be added to a poly-adenylation signal excised from bGH gDNA to create a larger poly-adenylation signal which includes non-genomic sequences. For example, if a genomic bGH gDNA sequence were obtained consisting of 50 nucleotides upstream and 50 nucleotides downstream from the 3' end, a non-genomic DNA compound might be ligated either upstream or downstream thereof (or both) in order to obtain a substantially larger DNA compound comprising a bGH polyadenylation signal in accordance with the present invention.

Finally, total or partial chemical synthesis is optionally employed to prepare any bGH polyadenylation signal described above.

For convenience in synthesis and isolation, the preferred embodiment of a bGH polyadenylation signal according to the present invention is the product obtained cleavage of bGH gDNA by the PvuII restriction endonuclease of αGH2R2. Alternatively, a somewhat longer bGH polyadenylation signal is conveniently obtained by digestion with PstI.

The second nucleotide sequence of the DNA compound refers to an amino acid coding nucleotide sequence of a gene, preferably a cDNA gene. Specifically the second nucleotide sequence comprises nucleotides which are ordered codons for the synthesis of a preselected polypeptides other than bGH. Alternatively, a genomic DNA may be utilized as the second nucleotide sequence, as well as other genes which contain introns or nucleotide sequences which do not code for amino acids. The selected polypeptide can include any polypeptide for which gene coding therefor is known or can be constructed by known techniques. i.e., partial or total chemical synthesis. Such polypeptides would, therefore, include proteins such as human serum albumin, the interferons and various analogs thereof, growth hormones other than bovine growth hormone, immunogenic proteins useful in vaccines, interleukin 2, and insulin. The preferred embodiment in accordance with the present invention utilizes the tissue plasminogen activator (tPA) cDNA as the second nucleotide sequence, that which encodes for a polypeptide, to create a recombinant DNA molecule capable of expressing tPA in higher eukoryatic cells. The cloning and expression of human tissue plasminogen activator cDNA in *E. coli* is known and described in Nature 301:214–221 (Jan. 20, 1983). The known methods represent useful means of obtaining tPA cDNA.

The first nucleotide sequence contains a promoter which is capable of initiating transcription of gene comprising the second nucleotide sequence by an RNA polymerase When the second nucleotide sequence is from a genomic source, the first nucleotide sequence may comprise a promoter already contained therewithin Alternatively, and especially when the second nucleotide sequence consists of cDNA, a distinct first sequence is selected and incorporated from a number of useful promoters which are known and readily available in genetic engineering applications These include the SV40 promoter (See Journal of Molecular and Applied Genetics 1:327–341 and references cited therein.) and the LTR promotor (See U.S. Pat. 4,405,712). The preferred promoter in accordance with the present specification is the CMV I.E. promoter, most preferably the fragment thereof derived from the Sau3A restriction endonuclease. The restriction endonuclease cleavage maps of the region of the human cytomegalovirus (CMV) genome containing the major immediate early gene (CMV I.E.) have been described in detail (Stinski, et al., J. Virology, 46:1–14, 1983., Stenberg, et al., J. Virology, 49:190–199, 1984; Thomsen, et al., Proc. Natl. Acad. Sci. USA, 81:659–663, 1984). These references describe a 2.0 kilobase PstI fragment which contains the promoter for the major immediate early gene. When this 2.0 kb PstI fragment is isolated and digested with Sau3AI, a 760 base pair fragment is obtained among the products. This 760 base pair fragment can be distinguished from the other products by its size and the presence of a SacI cleavage site and a BalI cleavage site within the fragment. Because of its convenient identification, utilization of this Sau3AI fragment is the preferred method of use of the CMV I.E. promoter as described in the present specification The locations of the first three sequences relative to each other is critical. The first sequence must be linked to the second which is linked to the third, each sequence must be in the proper orientation and each sequence must be in the same reading frame. When the three sequences are adjacently attached as such so that the polypeptide encoded by the second sequence may be produced, they are said to be operably linked.

The fourth nucleotide sequence optionally provides a selectable marker which can be utilized to determine whether the recombinant DNA compound has been incorporated into the expressed genetic material of a living cell. The use of such markers and the principles of selectivity therefor are well known and well recognized in the art. The nucleotide sequence which comprises the selectable marker operates essentially independent of the above described first, second and third sequences. Accordingly, the location of the fourth sequence in the DNA compound relative to the other three sequences is not critical. Selectable markers include antibiotic resistance genes which are useful to determine incorporation into those living cells towards whom the antibiotic is otherwise lethal. In mammalian cells, for example, the aminoglycoside antibiotic G418 results in inhibition of protein synthesis and death of the cell. Accordingly, the G418 resistance gene comprises a suitable selectable marker. Similarly, the dihydrofolate reductase (dhfr) gene provides a useful marker for cells (e.g., Chinese hamster ovary cells) which can be prepared dhfr deficient.

Another technique for selection which does not require the utilization of a marker on the DNA compound of the present invention is the use of co-transference techniques whereby both the DNA compound of the present invention absent a marker and a separate DNA molecule containing the marker are co-transferred into a cell. See U.S. Pat. 4,399,216, issued to the Columbia University. Incorporation into the expressed genetic material of a higher eukoryotic cell is accomplished by known means. Typically the incorporation will result in the presence of a DNA compound in the chromosomal structure of the cell, but may also be accomplished by an extra-chromosomal incorporation, e.g., utilization of a recombinant bovine papilloma virus. See N. Hsiung, et al., J. Molecular and Applied Genetics 2:497–506 (1984) for the methodology for such incorporation.

Although the summary of the invention refers to it as a circular recombinant DNA molecule, linear forms thereof exist as a result of cleavage, e.g., at specific sites by restriction endonucleases and more randomly by other nucleuses and the like. The present specification provides both the circular and linear recombinant DNA compounds as characterized above.

The present specification also provides the use of the recombinant DNA compound of the present invention for the expression of a preselected polypeptide. This use is accomplished by inserting the recombinant DNA compound into the expressed genetic material of a higher eukaryotic cell or cell line. These higher eukaryotes in accordance with the present invention consist of cells and cell lines derived from multi-cellular organisms, especially mammalian cells and cell lines. Culturing these cells or cell lines in accordance with known techniques then yields the pre-selected polypeptide, e.g., tissue plasminogen activator or tPA.

The present invention accordingly provides a novel use for a bGH polyadenylation signal in recombinant constructs prepared therewith. The charts herein further describe the construction and operation of the present invention. Conventions used to represent plasmids and fragments in Charts A-K, though unique to this application, are meant to be synonymous with conventional representations of plasmids and their fragments. Unlike the conventional circular figures, the single line figures on the charts represent both circular and linear double-stranded DNA with initiation or transcription occurring from left to right (5' to 3'). Asterisks (*) represent the bridging of nucleotides to complete the circular form of the plasmids. Linear pieces of double-stranded DNA do not have asterisk marks. Endonuclease restriction sites are indicated above the line. Gene markers are indicated below the line.

Thus, in the present specification, a DNA compound, i.e., a polymeric deoxyribonucleic acid wherein the sequence nucleotides thereof are selected from the group adenine (A), thymine (T), cytosine (C), and guanine (G), is depicted partially by a horizontal line. The line represents either a regular phosphodiester bond or discrete number of DNA residues. Unless these residues are further characterized or specified, e.g., by reference to the nucleotide sequence of a gene, promotor, marker, or endonuclease restriction enzyme site, the residues may be arbitrarily composed, subject only to the known limitations on size, location, and proximity to functionalized and/or characterized sequences of these uncharacterized intervening sequences. In other words, these intervening sequences must not negate the suitability of the resulting DNA compound for its intended purpose. More preferably, however, the intervening sequences will contain preselected and useful nucleotide sequences which will further enhance the intended purpose (e.g., enhance expression levels of a preselected polypeptide) or will permit selection in a broader range of hosts (e.g., by inclusion of antibiotic resistance genes). Hence, as represented herein by formula, the DNA compounds optionally include sequences of nucleotides having structural and/or functional characteristics in addition to those expressly designated.

In Charts A-K the following symbols are employed:

B = a bGH polyadenylation signal, possibly including related nucleotides.
F = nucleotides coding for a pre-selected polypeptide.
M = an optional selectable marker.
G = genomic bGH nucleotides, excluding those, if any, comprising bGH polyadenylation signal and related nucleotides designated above as the "B" region.
I = Genomic bGH intron (III).
T = tPA gene.
P = a preselected promoter, preferably the CMV I.E. promoter.
c = Cytosine tail.
N = Untranslated 5' region of renin.
R = Renin sequence.
dhfr = Dihydrofolate reductase.
SV400ri = SV40 promotor and origin of replication.
AmpR = Ampicillin resistance.
PSV40 = Promoter of SV40.

With respect to these charts, Chart A provides a generalized method for the preparation of DNA compounds according to the present invention. In accordance with Chart A, a plasmid pX containing nucleotides coding for a pre-selected polypeptide is digested with restriction endonucleases (arbitrarily designated as ResI and ResII in the chart) to yield a formula 1 DNA compound containing essentially the desired ordered codons for the polypeptide. The formula 1 is for example, preferably a cDNA compound coding for the polypeptide. When not conveniently available from a plasmid such as pX, total or partial chemical synthetic methods may be employed for constructing the formula 1 compound. Similarly, for formula 1 compounds lacking convenient restriction endonuclease sites, chemical modification by known methods is employed to arrive at the formula 1 compound.

The next construction in accordance with Chart A is the preparation of a formula 2 DNA compound containing a suitable marker. Accordingly, the plasmid pM with restriction endonuclease sites arbitrarily designated as ResII and ResIII are digested to yield a formula 2 compound containing a selectable marker.

The recombination of the formula 1 and formula 2 DNA compounds is then undertaken to yield a formula 3 DNA compound.

In order to incorporate a bGH polyadenylation signal into the formula 3 compound, a plasmid pbGH, containing bGH gDNA is digested with restriction endonucleases arbitrarily designated as ResIII and ResIV. This yields the formula 4 DNA compound containing a bGH poly-adenylation signal. Depending upon the exact ResIV which is selected, the formula 4 DNA compound will include an intron from the bGH gDNA. Chart A depicts the Res IV cleavage site within a range of locations. This range represents the variable lengths of the bovine growth hormone polyadenylation signal which may be employed in accordance with the present invention. Optionally, the product of digestion of plasmid pBGH with the restriction endonucleases may be further modified by digestion with other nucleuses to yield formula 4 polyadenylation signals. Alternatively, of course, the formula 4 compound may simply be derived by total or partial chemical synthesis by known methods.

The formula 3 compound is digested with ResI to allow for ingestion of the formula 4 compound downstream from the polypeptide codons.

Ligation of the formula 3 and formula 4 compounds will then yield a formula 5 plasmid. If the formula 3 compound does not include a promotion sequence, a DNA sequence comprising a promoter may be generated by digesting a plasmid, pZ, containing a selected promoter with Res V as depicted in formula 6. Formula 5 plasmid may then be digested with an appropriate restriction endonuclease, here ResII, and ligated to a formula 6 promoter to yield the DNA compound of formula 7. Formula 7 represents generally a DNA compound according to the present invention. The first DNA sequence of the present invention, that which provides the promoter, is represented in formula 7 as "P". Operably linked directly adjacent to the first sequence is the second nucleotide sequence, that which encodes for the preselected polypeptide to be produced. The second nucleotide sequence is represented in formula 7 as "F". The third nucleotide sequence, that which contains the bovine growth hormone polyadenylation signal, is located directly adjacent to the second sequence and operably linked thereto. In formula 7, the third nucleotide sequence is represented by "B". Finally, the fourth nucleotide sequence, that which contains the marker gene, is present in the DNA compound of the present invention in no critical relationship to the other three elemental sequences as it serves an unrelated function and operates independant of the above described operably linked functional unit. The fourth nucleotide sequence is represented by "M" in formula 7.

The order of steps in the assembly of the DNA compounds representing the components of the formula 7 compound is in general not critical and may be accomplished in whatever order most convenient based on available starting materials, etc. Accordingly, the method of Chart A, as well as the succeeding charts, may be modified to reflect variation in the order of assembly.

Chart B provides a convenient method for the preparation of a plasmid useful in obtaining a bGH polyadenylation signal for use in the preparation of the formula 7 DNA compound.

In accordance with Chart B, the plasmid pSV2dHR is digested with the appropriate endonucleases, EcoR1 and BamH1, as indicated in to yield the formula 8 DNA compound containing the ampicillin resistance gene (designated as Amp on Chart B) the SV40 origin and associated promoters, as well as the mouse dihydrofolate reductase (dhfr) gene. A description of the preparation and use of plasmid pSV2dHR is described by S. Subramani, et al., "Expression of the Mouse Dihydrofolate Reductase Complementary Deoxyribonucleic Acid in Simian Virus 40", Molecular and Cellular Biology 2:854–864 (Sep. 1981). Similarly, with respect to Chart B, the plasmid pGH2R2 is digested with the same restriction endonucleases, EcoR1 and BamHl to yield the formula 9 DNA compound containing genomic bovine growth hormone DNA sequence (bGH gDNA). The plasmid pNGH2R2 is derived from an E. coli HB101 host, NRRL Deposit Number B-15154. This plasmid is known in the art and readily produced by methods known in the art. See European published application 83306655.8, published on June 24, 1984. The formula 8 and formula 9 DNA compounds are then ligated to yield pSVCOW7 (formula 10).

Chart C describes the use of plasmid pSVCOW7, formula 10, in the preparation of DNA compounds according to the formulas 11, 12 and 13, which are then useful in the synthesis of the formula 19 and formula 20 compounds of Chart E. Thus, Chart C describes the preparation of the various formula 11, 12 and 13 compounds by digestion with restriction endonucleases as described as follows and in the chart. Formula 11 is generated by digesting formula 10 with EcoR1 and BamH1. The fragment depicted in formula 11 is the same fragment depicted in formula 8 in Chart B used to make a compound of formula 11. Formula 12 represents the fragment generated by the digestion of formula 10 with EcoR1 and PvuII. Fragment 12 contains the bovine growth hormone polyadenylation signal and a portion of the structural gene for bovine growth hormone. The portion of the structural gene present in formula 12 is represented by "G". Similarly, formula 13 represents the fragment generated by the digestion of formula 10 with EcoRI and PstI. The fragment according to formula 13 contains portions of the bGH structural gene including an intron. The structural gene portion present is represented by "G" except that part which makes up the intron which is represented by "I".

With respect to the formula 13 compound, the digestion with the EcoRI and PstI endonucleases is followed by the action of DNA polymerase at the PstI site in order to yield a Blunt-ended or fully base paired formula 13 compound.

The formula 12 and formula 13 compounds represent useful bGH polyadenylation signals in accordance with the present invention. The nucleotide sequences for these formula 12 and formula 13 compounds respectively comprise the ordered sequence set forth above for bGH gDNA from the PvuII cleavage site or the PstI (Blunt-ended) cleavage site through the end of the bases identified above for bGH structural gene gDNA.

Also in Chart C, the preparation of tPA cDNA from the plasmid pPSA18 is described. The preparation of this formula 14 plasmid is described below, in the Description of the Preferred Embodiments section, Preparation 2 subsection, including a detailed description of the modifications resulting in the BamHI and BalI restriction nucleuses at, respectively, the regions coding for the end terminal amino acids at the BamHI site.

Chart D provides the method whereby two plasmids are constructed, pTPA-IPA-dhfr (formula 16) and pTPA-PA-dhfr (formula 17) which respectively contain either the polyadenylation signal of formula 13 or of formula 12. By the method of Chart D, the formula 11 compound prepared in Chart C is ligated to the formula 15 compound of Chart C to yield a DNA compound which is then ligated either to the formula 13 polyadenylation signal or the formula 12 polyadenylation signal, respectively. The resulting products represent the intron-containing bGH polyadenylation signal of formula 16 and the compound of formula 17 whose bGH polyadenylation signal does not contain this intron.

Chart E describes the method by which the formula 19 (pIE-TPA-PA-dhfr) and formula 20 (pIE-TPA-IPA-dhfr) compounds containing useful promoters are prepared. In accordance with Chart E, the CMV I.E. promoter shown in formula 18 (a 760 base pair fragment obtained by digestion with the endonuclease Sau3AI) is ligated with the DNA compound produced by digestion of the formula 17 compound with the restriction endonuclease BamHI, followed by treatment with bacterial alkaline phosphotase. The fragment represented in formula 18 contains an internal SacI site which is useful in detecting recombinant compounds which contain the promoter fragment by providing a distinguishing restriction enzyme site. The resulting formula 19 compound represents a species within the scope of the formula 7 DNA compounds described in the present specification. Analogously, Chart E also describes the preparation of the formula 20 compound when the formula 16 compound is utilized in place of the formula 17 compound as a starting material.

The bGH polyadenylation signal of Formula 21 in Chart F are obtained as follows. Plasmid pSVB3/Ba containing a 2.2-kb Bam HI/EcoRI restriction fragment containing the entire bovine growth hormone gene along with 400 bp of its 3' flanking sequence is constructed as described in PNAS 81, 3944-3948 (July 1984). A series of deletions of surrounding sequences are made to obtain a minimum sufficient polyadenylation sequence which allows the accurate and efficient production of wild-type bGH 3. ends. The deletions are generated in two stages. A series of Bal-31 deletions extending from the EcoRI site at the juncture of the nucleotides coding for bGH and the pBR322 sequences upstream toward the 3' end of the polyadenylation site as described in PNAS 81 3944-3948 (July 1984) to give plasmid pSVB3/Ba #11 (Δ+20). The 5' boundary of the polyadenylation signal is defined in a similar manner utilizing the Sma I site in the pSVB3/Ba clone. The deletion yielding wild-type 3' ends contains 52 nucleotides of the 3' bGH specific sequence and extends to 10 nucleotides upstream from the hexanucleotide AA-TAAA. Chart F sets forth diagramatically the experimental detail of these deletions the general procedures being carried out by means known in the art. See, e.g., "Molecular Cloning, A Laboratory Manual," by T. Maniatis, et al., 1982.

The sizes of the deletions are determined by Sanger dideoxy sequencing. The accuracy of polyadenylation for each deletion mutant is determined by the transfection of Cos-1 cells by calcium phosphate precipitation followed by S1 mapping of the transiently expressed A RNAs. The efficiency of polyadenylation for each deletion as compared to wild-type (pSVB3/Ba) is roughly determined by Northern Blot analysis of the same A+RNAs. As represented by formula 21, the polyadenylation signal which accurately and efficiently directs polyadenylation consists of 52 nucleotides and includes 10 nucleotides upstream the AATAAA hexanucleotide through 18 nucleotides downstream from the polyadenylation site. In formula 21 the hexanucleotide and polyadenylation site are underlined.

By the general and specific methods described above, various circular recombinant DNA compounds of formula 7 are prepared using known and standard techniques in molecular biology. All of these formula 7 compounds may also be prepared in linear form wherein cleavage of a phosphodiester bond has been accomplished utilizing one of the known nucleuses.

These recombinant DNA compounds of formula 7 are usefully employed in the synthesis of a pre-selected polypeptide by incorporation into the expressed genetic material of a higher eukaryotic cell or cell line. As described above, this incorporation into the expressed genetic material of a higher eukaryotic cell or cell line is accomplished by methods known in the art, including, for example, transfection of a formula 7 compound. Once the expressed genetic material of the higher eukaryotic cell or cell line comprises the formula 7 compound, known techniques for culturing such cell lines are employed in order to obtain expression of the pre-selected polypeptide.

The pre-selected polypeptides so expressed are then recovered from the cell culture by conventional means. Each pre-selected polypeptide then can be used to accomplish known pharmacological uses therefor by known means. Alternatively, polypeptides are known to be nutritionally useful.

DESCRIPTION OF THE PREFERRED EMBODIMENTS

The present invention is more completely understood through the operation of the following preparations and examples. All methods herein for synthesis of DNA compounds, including plasmid construction are standard techniques well known to those of ordinary skill in molecular biology research. The techniques have, for example, been compiled in "Molecular Cloning: A Laboratory Manual" by T. Maniatis, et al., Cold Spring Harbor Laboratory, Cold Spring Harbor, N.Y., 1982.

Preparations

Preparation 1. Synthesis of Plasmid pSVCOW7.
Refer to Chart B.

The plasmid pSV2dhfr (prepared according to the procedure of S. Subramani, Molecular and Cellular Biology 2:854-864 (Sept. 1981) is digested with BamHI and EcoRI to yield the fragment according to formula 8 containing the ampicillin resistance gene, the SV40 origin, and the dhfr gene. The other fragment, represented by formula 9, results from digesting plasmid λGH2R2 with the same restriction endonucleases. Formula 9 represents DNA containing the genomic bovine growth hormone gene, i.e., bGH gDNA. Plasmid λGH2R2 is obtained from an E. coli HB101 host, NRRL B-15154. This resulting formula 9 bGH gDNA fragment is then ligated with the formula 8 compound to yield the formula 10 plasmid pSVCOW7.

Preparation 2 Synthesis of the Plasmid pPSA18.

A full length cDNA clone of human tissue plasminogen activator (tPA) is obtained or prepared Methods known in the art are utilized, e.g., Pennica, et al., Nature 301:214-221 (Jan. 20, 1983), for preparing tPA cDNA. The tPA cDNA is then cut with the restriction endonuclease HgaI and the ends treated with the DNA polymerase I klenow fragment. BamHI linkers are then ligated to the HgaI ends. The resulting cDNA is then cleaved with the restriction endonuclease NarI and the 490 base pair fragment is isolated which contains the coding sequences for the N-terminal amino acids of tPA. This DNA compound exhibits one NarI end and one HgaI end with the previously coupled BamHI linker. In a separate reaction, tPA cDNA is digested with both NarI and BglII. A 1650 base pair NarI/BglII fragment is isolated which contains the coding sequences for the C-terminal amino acids of tPA. The N-terminal and C-terminal fragments isolated above are then ligated to plasmid pKC7 (prepared by the method of Rao, et al., Gene 7:79-82, 1979) to yield the title plasmid pPSA18. This plasmid exhibits the entire coding region for tPA, with a unique BamHI cleavage site in the 5'-untranslated region of the coding region.

EXAMPLES

Example 1

Construction of Plasmids pTPA-PA-dhfr, pTPA-IPA-dhfr, pIE-TPA-PA-dhfr, and pIE-TPA-IPA-dhfr.

The assembly of the tPA expressing plasmids is accomplished in two steps as indicated below:

A. STEP 1. Refer to Charts C and D.

The following pieces of DNA were ligated together

1) An EcoRI/BamHI fragment (formula 11) from pSVCOW7 (formula 10), which is alternatively derived as the EcoRI/BamHI fragment from a parent plasmid pSV2dhfr (formula 8) available from Bethesda Research Laboratories. This fragment represented by formula 11 contains the origin of replication from pBR322 and an ampicillin resistance gene expressed in *E. coli*, which allow the plasmid to replicate in *E. coli*. The fragment also contains the mouse dihydrofolate reductase cDNA in a construction that allows expression in mammalian cells See Subramani, et al., Mol. Cell. Biol. 1:854–864 (1981).

2) A BamHI/BalI fragment (formula 15) from plasmid pPSA18 (formula 14), which contains the full coding region from tPA cDNA. The BamHI cut is in cDNA coding for the 5 untranslated sequences of the mRNA, and the BalI cut is in cDNA coding for the 3' untranslated region of the cDNA.

3) Two fragments each containing a bGH polyadenylation site are obtained as follows:

a) A PvuII/EcoRI fragment (formula 12) from pSVCOW7, which is entirely bovine DNA, extending from the PvuII site in the 3' most exon of the bGH gene, to the EcoRI site downstream from the 3' end.

b) A PstI/EcoRI (formula 13) fragment from pSVCOW7, which is entirely bovine DNA, extending from the PstI site in the fourth exon of the bGH gene, to the EcoRI site downstream from the 3' end.

The result of ligating the above fragments (1)-(2)-(3)(a) and (1)-(2)-(3)(b) is respectively two plasmids:

(a) pTPA-PA-dhfr (formula 17), which contains the tPA cDNA with the bGH polyadenylation region ligated to its 3' end.

(b) pTPA-IPA-dhfr (formula 16), which contains the tPA cDNA with a longer segment from the 3'-end of the bGH gene, including an intron, ligated to its 3'-end.

Both plasmids of formula 16 and formula 17 contain a unique BamHI cleavage site at the 5'-end of the tPA cDNA.

B. STEP 2. Refer to Chart E.

Both plasmids constructed in Step 1 are cleaved with BamHI, and a 760bp Sau3AI fragment containing the CMV immediate early promoter (formula 18) is ligated into the BamHI site. Plasmids containing the inserted fragment in an orientation such that transcription from the promoter would synthesize an mRNA for tPA are identified by cleavage of the plasmids with SacI. The resulting plasmids are:

(a) pIETPA-PA-dhfr (formula 19) contains the tPA cDNA insert with the CMV promoter linked on the 5'-end and the bGH polyadenylation signal linked on its 3'-end.

(b) pIETPA-IPA-dhfr (formula 20) is the same as (a) except, it contains a longer piece from the 3'-end of the bGH gene, including an intron.

Example 2

Transfection into Cells.

Both plasmids derived in Step 2 (Example 1) above are transfected into Chinese hamster ovary (CHO) cells deficient in dihydrofolate reductase (dhfr) using conventional transfection techniques. This cell line is mutant DXB-11 from L. Chasin, Columbia University (Proc. Nat.. Acad. Sci. USA 77:4216.4220 1980).

The above methods for transfection utilizes calcium phosphate transfection of DNA into cells described in detail by Graham, et al. (Introduction of Macromolecules into Viable Mammalian Cells, Alan R. Liss Inc., N.Y., 1980, pp. 3.25). Cells which incorporate the transfected plasmids are selected based on dhfr deficiency by growth in Dulbecco's modified Eagle's medium plus proline.

Although the Chinese ovary cells are especially adapted for use with a plasmid such as those formula 19 and formula 20 compounds constructed above, the use of the CMV I.E. promoter and bGH polyadenylation site in the tPA gene expression does not depend on use of the dhfr marker on these plasmids. Expression of cDNA genes is also obtained with different selectable markers, such as gene which confers resistance to antibiotic G418 (J. Mol. Appl. Genet. 1:. 327–341, 1982) and in other cell lines with an alternate marker replacing the dhfr marker. Accordingly, such a replacement permits the use of many different cell lines as hosts for the plasmids.

Example 3 tPA Expression.

From the cells transfected with pIETPA-PA-dhfr, clones are isolated, which, when grown in a monolayer for two days, synthesize at least 100 ng tPA per million cells. From cells with pIETPA-IPA-dhfr, clones are isolated which synthesize at least 10 ng tPA per million cells. Accordingly, the present specification provides a method for obtaining the necessary polyadenylation of messenger RNA, especially for transcription from cDNA genes coding for the pre-selected polypeptide. This permits the use of such cDNA genes for expression in higher eukaryotic cells and particularly provides such expression in surprisingly and unexpectedly high yield.

Example 4

When following the procedure described above in Example 1 Part A, fragments generated in subparts (1) and (2) are ligated with the nucleotide sequence of formula 21 of Chart F to yield a plasmid identified as pTPA-52PA-dhfr (formula 22) which contains the tPA cDNA is obtained which has the 52 nucleotide base pair polyadenylation region of formula 21 ligated to its 3' end.

When following the procedure described in Example 1 Part B, (insertion of the CMV IE promoter fragment), the plasmid represented by formula 22 is substituted for the plasmids of formula 16 and 17 to yield the plasmid pIE-TPA-52PA-dhfr is obtained which contains the tPA cDNA with the CMV promoter on the 5'-end and the 52 base nucleotide bGH polyadenylation signal of formula 21 on its 3' end.

When the plasmid of pIE-TPA-52PA-dhfr is substituted for the plasmids of formula 19 and 20 in the procedures of Example 2 and Example 3 and the general procedure thereof followed, expression of tPA is achieved.

The compound of formula 23 in Ghart F is to obtained by subjecting plasmid pSVB3/Ba (formula 22) to the following steps: 1) Small digestion, 2) Ba131, 3) Fill in with T4 Polymerase, 4) ligate Sma linkers, and 5) Small digestion. In formula 23, ". . ." represents Ba131 deletions. The compound of formula 23 is thus a linearized and modified form of the compound of formula 22. Small is used to linearize the compound. Ba131 is then used to degrade or "chew back" the DNA at the ends generated by the Small digestion. Small sites are incorporated into the ends by ligation and digestion of Small linkers. Thus, compounds according to formula 23 represent various compounds which are generated by the Ba131 degradation process. The amount of degradation which takes place is determined by the concentrations and conditions present in the Ba131 treatment.

The compound of formula 24 is obtained by subjecting the compound of formula 23 to the following steps: 1) BamHI digestion, 2) BAP treatment, 3) gel isolation. The compound of formula 25 is obtained by subjecting the compound of formula 22 to the following steps: 1) SmaII digestion, 2) BamHI digestion, and 3) gel isolation. The compounds of formulae 24 and 25 are ligated to generate the compound represented by formula 26 wherein "" represents Bal31 deletions.

Example 5

Expression of Human Resin by Chinese Hamster Ovary Cells.

The expression of resin in CHO dhfr− cells followed the following strategy:

1) Insertion of a unique restriction site in the DNA coding for the 5′-untranslated region of resin mRNA;

2) Fusion of the bovine growth hormone (bGH) polyadenylation signal to DNA coding for the 3′-untranslated region of resin mRNA;

3) Insertion of the renin-bGH fusion into a vector (pSV2dhfr) with the selectable marker dihydrofolate reductase (dhfr);

4) Insertion of a promoter upstream from the resin gene; and,

5) Transfection of the resin expression unit into CHO cells.

Sizes are estimated by agarose gel electrophoresis.

1) Insertion of a unique restriction site in the DNA coding for the 5′-untranslated region of resin mRNA.

i. Construction of pRnPSI (refer to Chart G). Plasmid pRnPSI is a construction of two fragments: the PstI/SacI fragment (1.4kb) from pHRn321 represented by formula 27 containing the resin cDNA and the PstI/SacI fragment (2.7kb) from pUC12 represented by formula 28 (available from Pharmacia/PL). These two fragments are isolated by electrophoresis and ligated to construct pRnPSI (4.1kb) represented by formula 29. Plasmid pHRn321 is prepared as described in PNAS, U.S.A., 80 7405-7409 (1983).

ii. Construction of pRnBam. Plasmid pRnPSI lacks a con. venient restriction site for the removal of the remaining G/C tail which would otherwise interfere with transcription. The following steps take advantage of a fortuitous sequence 3′ to the G/C tail. These steps introduce a single site mutation at nucleotide -28 of the untranslated portion of the resin sequence. The mutation creates a unique BamHI site at a point 5′ to the prorenin sequence. The -28 position is in the untranslated region of the sequence as published in PNAS, U.S.A., 80. 7405-7409 (1983).

As shown in Chart H, plasmid pRnPSI is digested with PstI plus HindIII yielding a 4.7kb fragment represented by formula 30 and treated with 1 unit lambda exonuclease per picomole of ends of DNA. As depicted in formula 30, the fragment contains a Cytosine tail represented by "c", untranslated 5′ regions of resin sequence represented by "N", and translated portions of resin sequence represented by "R". Samples are removed after 3, 6, 10, and 15 minutes of digestion under conditions recommended by the supplier (New England BioLabs). The reaction products are combined, phenol extracted, and ethanol precipitated. The desired reaction products have a 3′ overhang comprising a portion of the resin coding sequence.

Mutagenesis was conducted in a final reaction volume of 50 microliters by first denaturing the DNA in water at 50° C. for 5 minutes. Five microliters of 10x annealing buffer (lx is 6 mM Tris, pH 7.4, 0.1 NaCl, 6 mM MgC12) and a 10 fold molar excess of a 15 base synthetic oligonucleotide comprised of 15 bases is added. The oligonucleotide will introduce a cytosine at position −28 and is otherwise complementary to nucleotides −35 through −20 of the 5′ untranslated region of the resin sequence as reported in PNAS, U.S.A., 80. 7405-7409 (1983). The mixture is slowly equilibrated to 10° C. at which point deoxynucleotide triphosphates were added to 0.4 mM each, along with 100 microcuries of tritiated dCTP and 5 units of DNA polymerase Klenow fragment which eliminates the 3. overhang and fills in the gap 3′ of the synthetic sequence. The reaction is shifted to 16° C. for 30 minutes, and then to 23° C. for 60 minutes. EDTA is added to 10 mM, and the DNA is phenol extracted and ethanol precipitated. The mutagenized heteroduplex is ligated using T4 DNA ligase (New England BioLabs) as recommended by the supplier generating a circular plasmid represented by formula 31

The DNA is transformed into E. coli DH1 (obtainable from ATCC). The E. coli in replicating the heteroduplex will create two populations of plasmids with half carrying the unique BamHI site and the other half having the original sequence in the 5′ untranslated region of resin. Those plasmids having the unique BamHI site are designated pRnBam.

2) and 3) Construction of pDPRnPAl: Fusion of the bovine growth hormone (bGH) polyadenylation signal to DNA coding for the 3′-untranslated region of resin mRNA; and insertion of the resin-bGH fusion into a vector (pSV2dhfr) having the selectable marker dihydrofolate reductase (dhfr).

Construction of pDPRnPAI involves a three-way ligation as described below.

(a) The construction of the pSVCOW7 is described above and diagrammed in Chart B. First the plasmid pSV2dhfr is obtained from the American Type Culture Collection or is prepared according to the procedure of S. Subramani, et al., Molecular and Cellular Biology 2:854-864 (1981). Plasmid pSV2dhfr is then digested with BamHI and EcoRI to yield 5.Okb fragment represented in Chart I by formula 32 containing the ampicillin resistance gene, the SV40 origin, and the dhfr gene. Next λGH2R2 which is obtained from E. coli NRRL B-15154 is digested with BamHI and EcoRI to obtain a 2.lkb fragment represented by formula 33 containing the genomic bovine growth hormone gene, i.e., bGH gDNA including the polyadenylation signal. The fragments in formula 32 and formula 33 are ligated to obtain pSVCOW7 shown in formula 34.

Plasmid pSVCOW7 is cut with PvuII and EcoRI to yield a 0.6kb fragment represented in Chart J by formula 35 containing the bGH polyadenylation signal for pDPRnPAl.

Plasmid pRnBam is cut with SacI, which cuts in DNA coding for the 3′-untranslated region of resin mRNA. The SacI end is converted to a blunt end with Klenow DNA polymerase. The plasmid is then cut with BamHI, and the 1.35kb fragment represented by formula 36 purified by gel electrophoresis and isolated.

The third fragment is obtained from pSV2dhfr Plasmid pSV2dhfr is cut with EcoRI plus BamHI, and a 5.Okb fragment represented by formula 37 is isolated by gel electrophoresis. The three isolated fragments shown as formulas 35, 36 and 37 ligated to generate plasmid pDPRnPAl (7.0kb) represented by formula 38.

4) Construction of pSVDPRnPA33. Insertion of a promoter.

Plasmid pSV2dhfr is cut with PvuII plus HindIII, and the 0.325kb fragment having thenormal case promoter (PSV40) is isolated by gel electrophoresis. The ends are made blunt with Klenow DNA polymerase, and BamHI linkers added. The resulting fragment is represented in Chart K by formula 39.

Plasmid pDPRnPAl are digested with BamHI and the ends dephosphorylated with +E. coli alkaline phosphatase to yield a linear fragment represented by formula 40.

The two fragments are ligated to form a circular plasmid. In the case where the fragments are oriented to direct expression of resin by the SV40 early promoter as shown in formula 41, the plasmid is named pSVDPRnPA33.

5) Transfection.

The plasmid pSVDPRnPA33 was transfected into Chinese hamster ovary cells deficient in dihydrofolate using traditional techniques.

From these transfections it is possible to isolate cells producing at least 2 pmoles of resin per ml culture fluid from a confluent monolayer after 2 days of growth. Methods are well known to adapt these cells to growth in the presence of methotrexate to increase the level of resin expression.

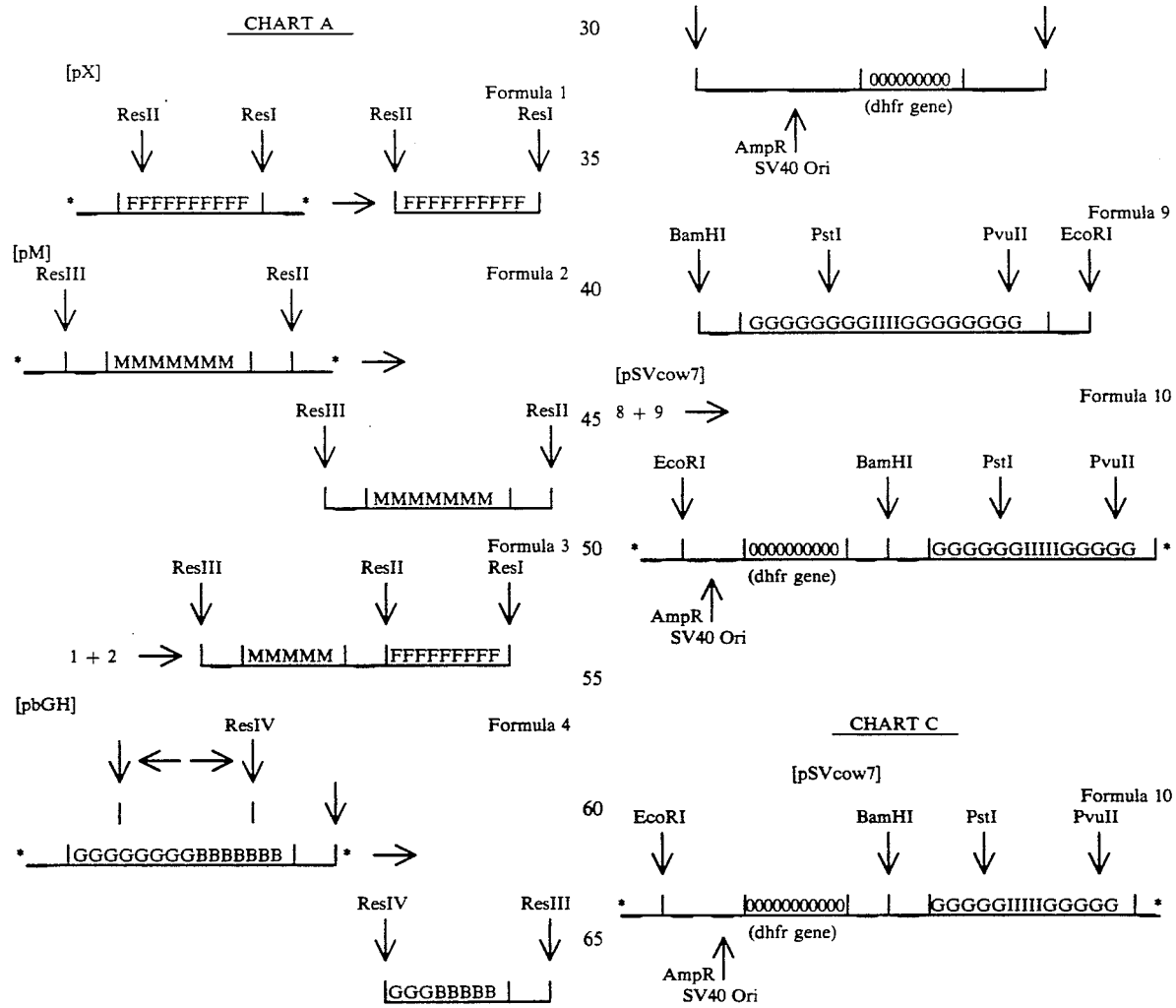

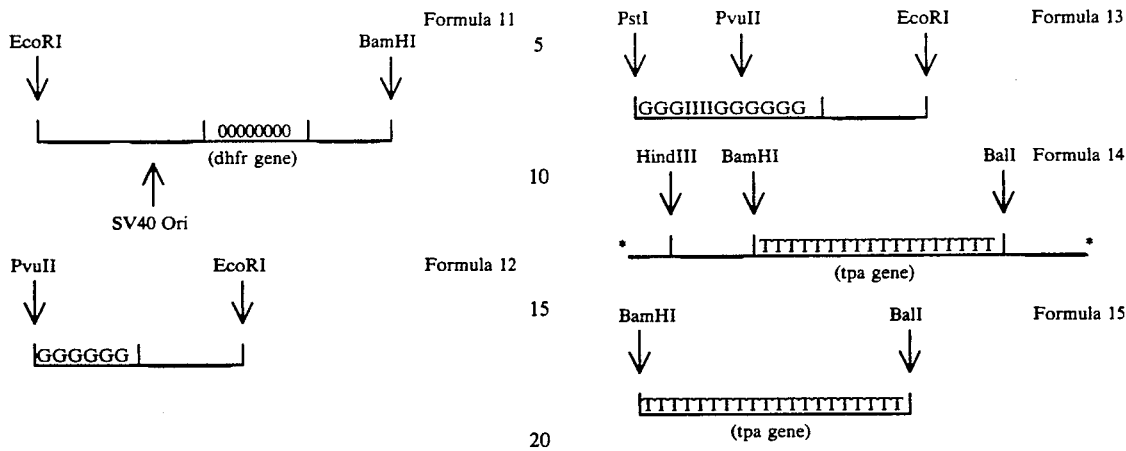
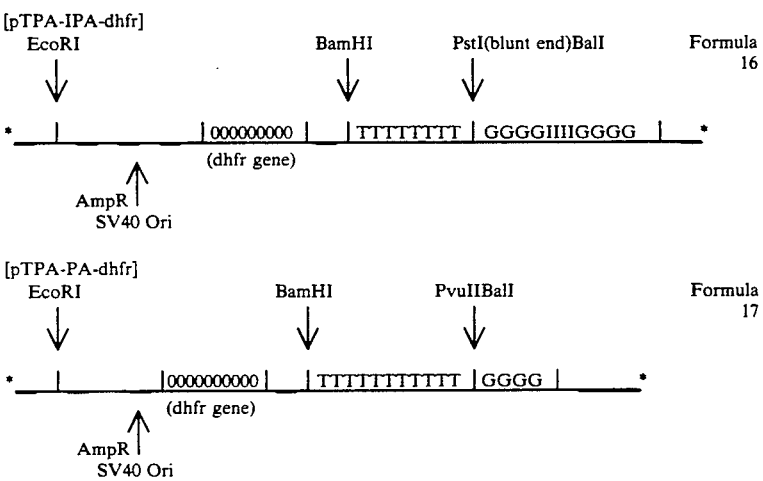
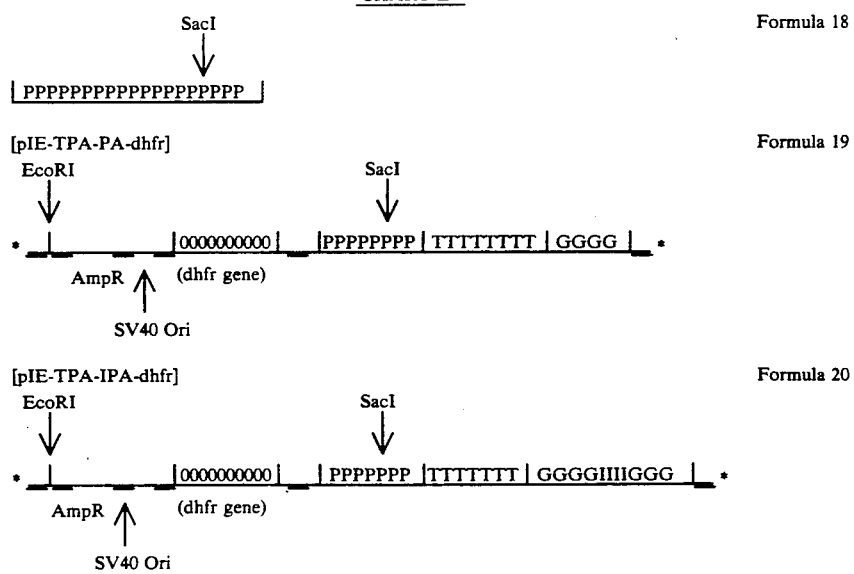

CHART F
5'  GTCCTTTCCTAATAAAATGAGGAAATTGCATCGCATTGTCTGAGTAGGTGTC  3'    Formula 21
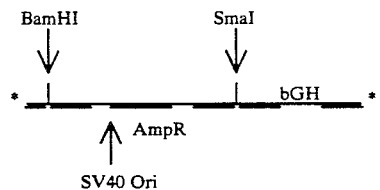
Formula 22
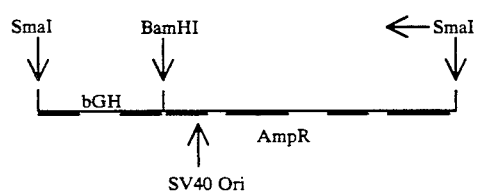
Formula 23
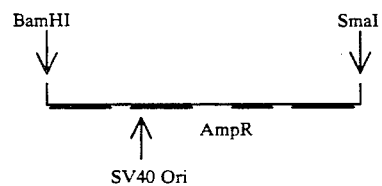
Formula 24
Formula 25
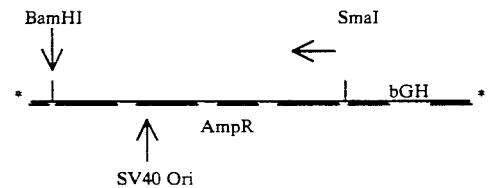
Formula 26
CHART G
Formula 27
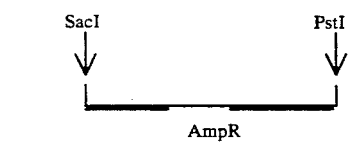
Formula 28
Formula 29
CHART H
Formula 30
-continued
CHART H
Formula 31
CHART I
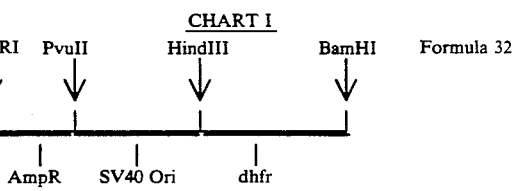
Formula 32
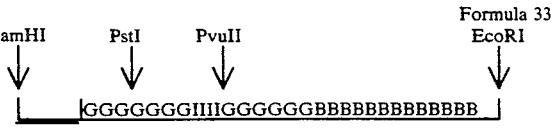
Formula 33

CHART I

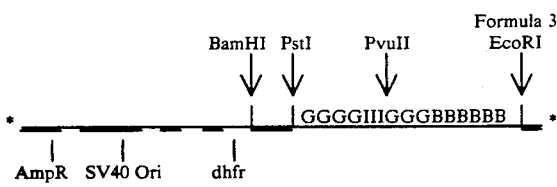

CHART J

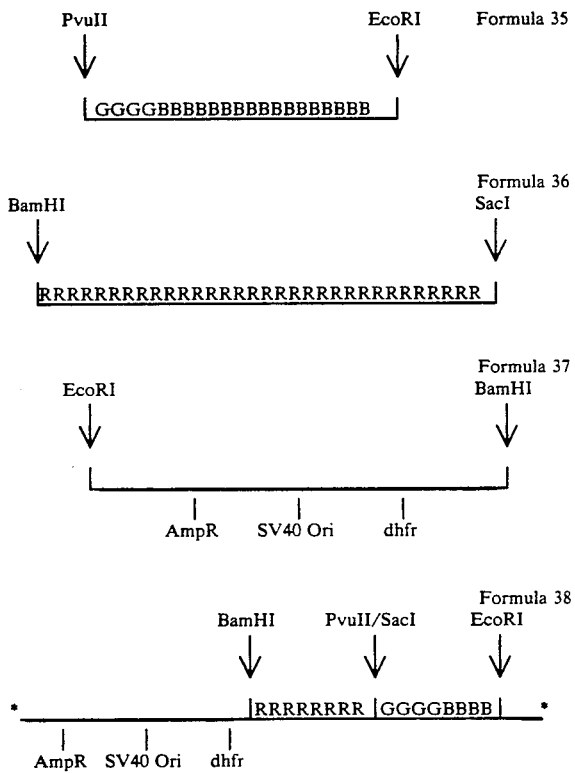

CHART K

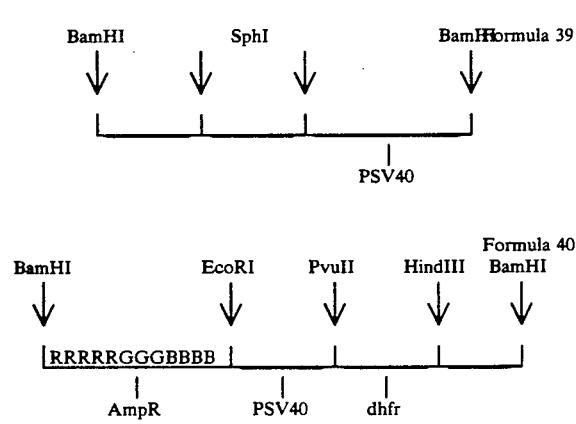

CHART K —continued

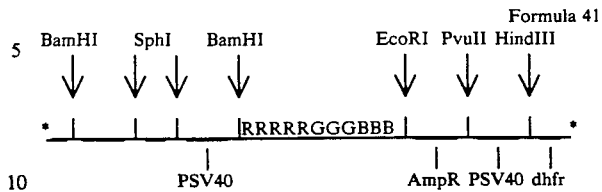

We claim:

1. A recombinant DNA molecule comprising:
   (a) a DNA sequence that encodes a polypeptide other than bovine growth hormone; and,
   (b) a bovine growth hormone gene polyadenylation signal, said polyadenylation signal comprises the nucleotide sequence:

5'GTCCTTTCCTAATAAAATGAGGAAATT-
   GCATCGCATTGTCTGAGTAGGTGTC 3';

wherein said DNA sequence that encodes a polypeptide other than bovine growth hormone is upstream from and operably linked to said polyadenylation signal.

2. A recombinant DNA molecule according to claim 1 further comprising a promoter, said promoter is upstream from and operably linked to said DNA sequence that encoders a polypeptide other than ovine growth hormone.

3. A recombinant DNA molecule according to claim 1 further comprising a selectable marker.

4. A recombinant DNA molecule according to claim 2 wherein said promoter is a Cytomegalovirus immediate early promoter.

5. A recombinant DNA molecule according to claim 1 wherein said polyadenylation signal comprises bovine growth hormone genomic DNA nucleotide sequence from the PvuII cleavage site in the condons coding for amino acids 190-192 to the next subsequent EcoRI cleavage site downstream therefrom.

6. A recombinant DNA molecule according to claim 5 wherein said polyadenylation signal comprises bovine growth hormone genomic DNA nucleotide sequence from the PstI cleavage site in the codons coding for amino acids 90-91 to the next subsequent EcoRI cleavage site downstream therefrom including the intron therein.

7. A recombinant DNA molecule according to claim 1 wherein said DNA sequen e that encodes a polypeptide other than obvine growth hormone comprises cDNA encoding tissue plasminogen activator.

8. A method of producing a pre-selected polypeptide which comprises the steps of:
   (a) culturing a eukaryotic cell or cell line comprising a recombinant DNA molecule according to claim 2, wherein said DNA sequence that encodes a polypeptide other than bovine growth hormone encodes a pre-selected polypeptide; and
   (b) recovering said pre-selected polypeptide.

9. The method according to claim 8 wherein the pre-selected polypeptide is tissue plasminogen activator.

10. A eukaryotic cell or cell line comprising a recombinant DNA molecule according to claim 1 wherein said eukaryotic cell or cell ine expresses said DNA sequence that encodes a polypeptide other than bovine growth hormone.

11. A eukaryltic cell o cell line according to claim 10 wherein said coding sequence is tissue plasminogen activator.

* * * * *